United States Patent
Kato

(10) Patent No.: US 9,839,794 B2
(45) Date of Patent: Dec. 12, 2017

(54) PARTICLE BEAM THERAPY APPARATUS

(71) Applicant: Mitsubishi Electric Corporation, Chiyoda-ku, Tokyo (JP)

(72) Inventor: Masayuki Kato, Tokyo (JP)

(73) Assignee: MITSUBISHI ELECTRIC CORPORATION, Chiyoda-Ku, Tokyo (JP)

(*) Notice: Subject to any disclaimer, the term of this patent is extended or adjusted under 35 U.S.C. 154(b) by 0 days.

(21) Appl. No.: 15/303,895

(22) PCT Filed: Jul. 14, 2014

(86) PCT No.: PCT/JP2014/068699
§ 371 (c)(1),
(2) Date: Oct. 13, 2016

(87) PCT Pub. No.: WO2016/009471
PCT Pub. Date: Jan. 21, 2016

(65) Prior Publication Data
US 2017/0028222 A1 Feb. 2, 2017

(51) Int. Cl.
*A61N 5/10* (2006.01)
(52) U.S. Cl.
CPC .............. *A61N 5/1071* (2013.01); *A61N 5/10* (2013.01); *A61N 5/1048* (2013.01); *A61N 5/1077* (2013.01); *A61N 5/1064* (2013.01); *A61N 2005/1074* (2013.01); *A61N 2005/1087* (2013.01)
(58) Field of Classification Search
CPC ...... A61N 5/10; A61N 5/1048; A61N 5/1064; A61N 5/1071; A61N 2005/1074; A61N 2005/1087; G21K 5/04; G21K 5/10
See application file for complete search history.

(56) References Cited

U.S. PATENT DOCUMENTS

| 9,415,241 | B2* | 8/2016 | Ito ........................... A61N 5/103 |
| 2007/0051905 | A1* | 3/2007 | Fujimaki .................. H05H 7/10 250/492.3 |
| 2007/0252093 | A1* | 11/2007 | Fujimaki .............. A61N 5/1048 250/492.3 |
| 2013/0231517 | A1 | 9/2013 | Iwamoto et al. |
| 2014/0086390 | A1* | 3/2014 | Nakatsugawa ........ A61B 6/487 378/62 |

FOREIGN PATENT DOCUMENTS

JP 58-190788 A 11/1983
JP 62-284284 A 12/1987

(Continued)

OTHER PUBLICATIONS

Office Action dated Sep. 21, 2016, by the Taiwanese Patent Office in corresponding Taiwanese Patent Application No. 103141572 and English translation of the Office Action. (5 pages).

(Continued)

*Primary Examiner* — David E Smith
(74) *Attorney, Agent, or Firm* — Buchanan Ingersoll & Rooney PC

(57) ABSTRACT

For the purpose of providing a particle beam therapy apparatus which is unnecessary to be separately verified for operational integrity of its dose monitors and is unnecessary to have an additional failure diagnosis function, a particle beam therapy apparatus is so configured that, by a dose-monitoring system controller, the main and sub roles of two dose monitors are switched therebetween at every radiation and their corresponding dose monitor circuits are controlled accordingly, so that operation checking of the two dose monitors can be performed during a therapeutic flow, without the need of a special operation.

4 Claims, 3 Drawing Sheets

(56) References Cited

FOREIGN PATENT DOCUMENTS

| JP | 2-82439 A | 3/1990 |
|---|---|---|
| JP | 2011-120810 A | 6/2011 |
| JP | 2012-42415 A | 3/2012 |

OTHER PUBLICATIONS

International Search Report (PCT/ISA/210) dated Aug. 19, 2014, by the Japanese Patent Office as the International Searching Authority for International Application No. PCT/JP2014/068699.

Website open resource by Medipolis Cancer Particle Beam Therapy Research Center, Japan [now, Medipolis Proton Therapy and Research Center, Japan], Introduction of particle beam therapy: "Particle Beam Therapy Apparatus", "5. Irradiation-System Devices (Beam Line Devices) for Forming Proton Beam Into Target Shape", "4. Dose Monitor", [searched on May 14, 2014] via Internet <URL: http://www.medipolis-ptrc.org/patient/facilities/overview/#device5/.

Office Action dated May 19, 2017, by the Taiwanese Patent Office in corresponding Taiwanese Patent Application No. 103141572 and English translation of the Office Action. (8 pages).

Office Action (Notification of Reason for Refusal) dated Jan. 31, 2017, by the Japanese Patent Office in corresponding Japanese Patent Application No. 2016-534004 and English translation of the Office Action. (7 pages).

\* cited by examiner

| Notification of the operation from the dose monitor circuit of the main dose monitor A | Notification of the operation from the dose monitor circuit of the sub dose monitor B | Notification of the operation about the dose monitor circuit of the main dose monitor A from the beam controller | Notification of the operation about the dose monitor circuit of the sub dose monitor B from the beam controller | Failure Determination |
|---|---|---|---|---|
| Provided | None | Provided | None | · The main dose monitor A and the dose monitor circuit of the dose monitor A are normal<br>· Communication between the dose monitor circuit of the dose monitor A and the beam controller is normal |
| None | Provided | None | Provided | · The dose monitor A or the dose monitor circuit of the dose monitor A is abnormal<br>· The sub dose monitor B and the dose monitor circuit of the dose monitor B are normal |
| Provided | None | None | None | · Failure in the beam controller<br>· Communication failure of the dose monitor circuit of the main dose monitor A or the beam controller, or between the dose monitoring system and the controller |
| Provided | Provided | None | None | · Failure in the beam controller<br>· Communication failure of the dose monitor circuit of the main dose monitor A, the dose monitor circuit of the sub dose monitor B or the beam controller, or between the dose monitoring system and the controller |

FIG. 3

PARTICLE BEAM THERAPY APPARATUS

TECHNICAL FIELD

The present invention relates to a particle beam therapy apparatus for performing cancer therapy or the like, through radiation of a particle beam.

BACKGROUND ART

In the radiation medical field for the purpose of cancer therapy, there have been advanced, development of a particle beam therapy apparatus that is a cancer therapy apparatus using proton or a heavy ion, and construction of a facility in which the therapy is performed using the particle beam therapy apparatus. According to the therapy by a particle beam using proton, a heavy ion, etc., a cancer diseased site can be irradiated in a concentrated manner as compared to the conventional radiation therapy using an X-ray, a γ-ray, etc., and thus it is possible to perform the therapy without influencing normal cells.

In recent years, with respect to the particle beam therapy apparatuses, high-level three-dimensional irradiation methods that can reduce influence on normal cells, such as a scanning irradiation method and a layer-stacking conformal irradiation method, are developed and put into practical use. According to the high-level three-dimensional irradiation methods, the beam condition is finely changed during irradiation to thereby execute a more precious control of dose distribution than otherwise.

The particle beam therapy apparatus is configured with treatment rooms each having an irradiation device for irradiating a patient with a specified particle beam according to a treatment plan, and an accelerator for generating the particle beam and transporting the beam under a specified beam condition to the designated treatment room, in response to a particle-beam request from the treatment room.

Furthermore, the irradiation device includes a dose monitoring system that performs monitoring for controlling so that the patient is irradiated with the particle beam by a prescribed dose amount. Since the irradiation dose is one of the particularly important treatment parameters, the dose monitor in the dose monitoring system of the particle beam therapy apparatus is generally made redundant, to thereby enhance the reliability thereof.

For the conventional particle beam therapy apparatuses, such a technique is known in which a dose monitor for measuring the irradiation dose is duplicated by providing a main dose monitor and a sub dose monitor in beam line devices through which a proton beam passes (for example, Non-Patent Document 1).

CITATION LIST

Non Patent Document

Non-Patent Document 1: Website open resource by Medipolis Cancer Particle Beam Therapy Research Center, JAPAN [now, Medipolis Proton Therapy and Research Center, JAPAN], Introduction of particle beam therapy: "Particle Beam Therapy Apparatus", "5. Irradiation-System Devices (Beam Line Devices) For Forming Proton Beam Into Target Shape", "4. Dose Monitor", [searched on 14 May, 2014] via Internet <URL: http://www.medipolis-ptrc.org/device_2.html>.

SUMMARY OF THE INVENTION

Problems to be Solved by the Invention

The dose monitor detects an amount of charges produced by the beam passing through a sensor portion of the dose monitor to thereby measure a dose amount of the beam passing therethrough. As previously described, the dose monitor has an important role of monitoring a radiation dose to be applied to the patient, so that its reliability is enhanced by multiplexing in order to prevent the patient from being seriously damaged immediately by a failure of the dose monitor.

In general, the system including two dose monitors is configured with: a main dose monitor for performing interruption of the beam upon detection of an administration dose value planned by a treatment plan system; and a sub dose monitor for performing interruption of the beam upon detection of a protective-interruption dose value that is larger by several % than the administration dose value, to thereby prevent excessive irradiation at the time of operational failure of the main dose monitor.

Although the main dose monitor and the sub dose monitor are functionally equivalent to each other except for their set dose values and the arrangement of their sensor portions for monitoring, their main and sub roles are generally fixed. Thus, so long as there is nothing wrong with the main dose monitor, such a case generally does not arise in which the sub dose monitor detects the protective-interruption dose value to thereby perform the interruption. However, there is a problem that, if multiple failures occur such that a failure of the main dose monitor occurs in an overlapping manner during a failure of the sub dose monitor in its dose detection function or beam interruption function, this causes a serious situation that may immediately results in excessive irradiation.

This invention has been made to solve the problem as described above, and an object thereof is provide a particle beam therapy apparatus which is unnecessary to be separately verified for operational integrity of the dose monitors and is unnecessary to have an additional failure diagnosis function.

Means for Solving the Problems

A particle beam therapy apparatus of the invention is characterized by comprising: an accelerator that emits a particle beam after accelerating it using a synchrotron; an irradiation device that radiates the particle beam emitted from the accelerator to an irradiation target; a first dose monitor and a second dose monitor each for detecting a dose amount of the particle beam radiated from the irradiation device; and a dose-monitoring system controller that controls the first dose monitor and the second dose monitor by assigning a first role of detecting a dose amount corresponding to an administration dose value and a second role of detecting a dose amount corresponding to an interruption dose value, to these monitors in a switched manner therebetween at every radiation.

Effect of the Invention

According to the invention, because of the configuration in which, by the dose-monitoring system controller, the roles of the two dose monitors are switched therebetween at every radiation and their corresponding dose monitor circuits are controlled accordingly, operation checking of the two dose monitors can be performed during a therapeutic flow, without the need of a special operation. Further, it becomes possible to certainly detect and specify a failure portion by two radiation steps unless these monitors both fail at the same time.

BRIEF DESCRIPTION OF THE DRAWINGS

FIG. 3 is a diagram showing examples of failure diagnosis by the dose-monitoring system controller in the particle beam therapy apparatus according to Embodiment 1 of the invention.

MODES FOR CARRYING OUT THE INVENTION

Embodiment 1

Figure 1:
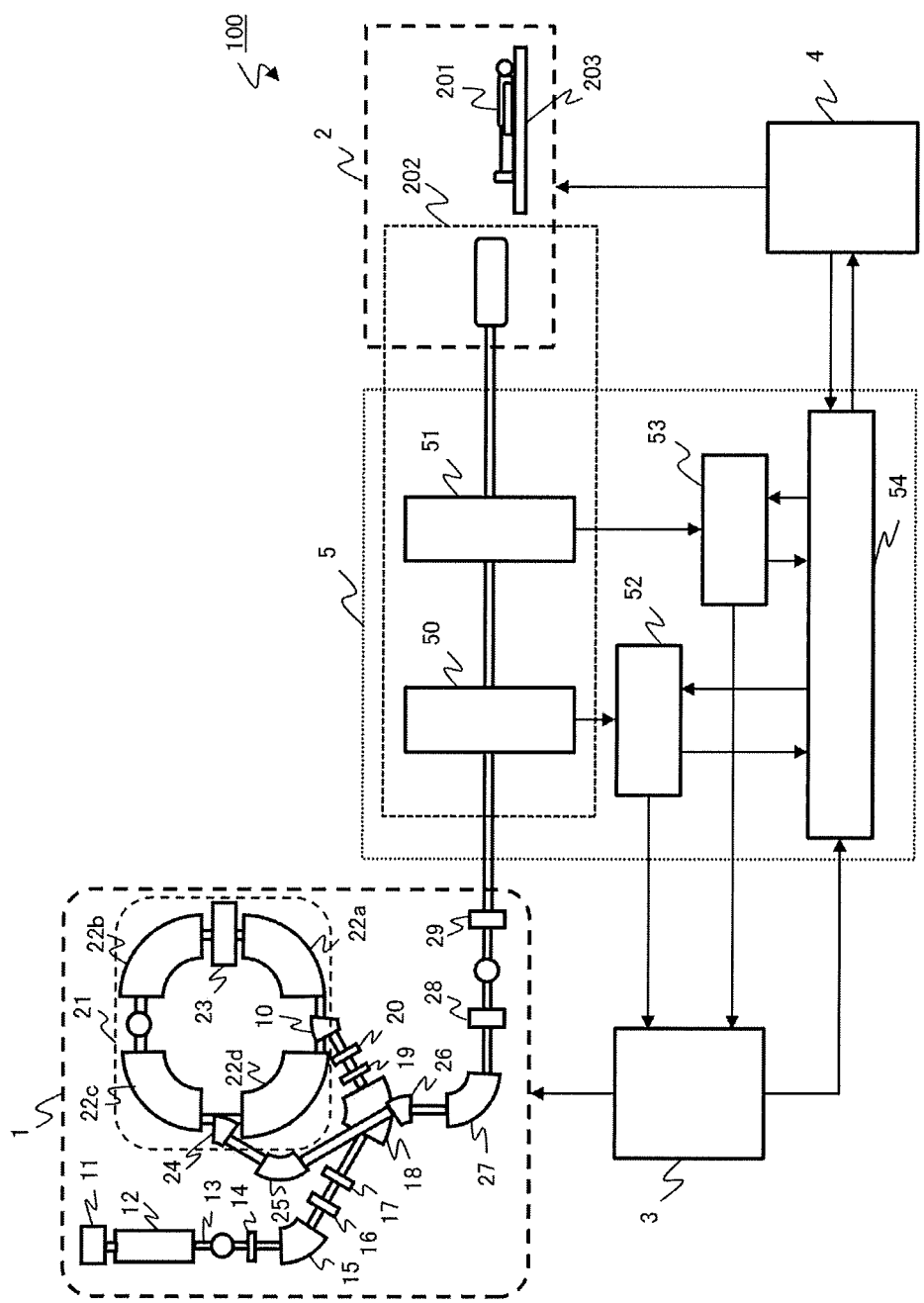
FIG. 1 is a configuration diagram showing a configuration of a particle beam therapy apparatus according to Embodiment 1 of the invention.

FIG. 1 is a diagram showing a configuration of a particle beam therapy apparatus according to Embodiment 1 of the invention. As shown in FIG. 1, an accelerator 1 and a treatment room 2 constitute a particle beam therapy apparatus 100 of Embodiment 1. Emission of the beam from the accelerator 1 is controlled by a beam controller 3. A patient 201 that is an irradiation target and irradiation devices 202 are placed in the treatment room 2, and the irradiation devices 202 are controlled by an irradiation controller 4. A dose monitoring system 5 is a component for constituting the irradiation devices 202.

The dose monitoring system 5 is configured with: a dose monitor 50 as a first dose monitor and a dose monitor 51 as a second dose monitor that are provided in two sets with dose monitor circuits 52, 53 as respective control circuits of the dose monitor 50 and the dose monitor 51; and a single dose-monitoring system controller 54.

The dose monitor 50 and the dose monitor 51 in the dose monitoring system 5 are connected to the dose monitor circuit 52 and the dose monitor circuit 53, respectively. The dose monitor circuit 52 and the dose monitor circuit 53 are each connected to the dose-monitoring system controller 54 and the beam controller 3, and the dose-monitoring system controller 54 is further connected to the irradiation controller 4 and the beam controller 3.

Next, basic operations of the accelerator 1 land in the treatment room 2 will be described. In FIG. 1, a particle beam that is an aggregation of ions (for example, hydrogen ions or carbon ions) generated by an ion source 11 of an injector 10 is subjected to pre-acceleration by a linear accelerator 12 prior to the injector 10 and is thus accelerated up to a specified kinetic energy. The pre-accelerated particle beam passes through a vacuum duct 13 in a low-energy beam transport system and is then introduced into a synchrotron 21 while being deflected, being converged-diverged, and being corrected in its trajectory, by the electromagnets 14 to 20.

In the synchrotron 21, electromagnets 22 (22a, 22b, 22c, 22d) are set so that the particle beam has a circulating orbit in the synchrotron 21, and the particle beam repeatedly receives an acceleration electric field formed by a high-frequency acceleration cavity 23. The particle beam is repeatedly accelerated by the acceleration electric field in the high-frequency acceleration cavity 23, so that its kinetic energy becomes higher with its acceleration. As the kinetic energy becomes higher, an intensity of magnetic field required for deflection of the particle beam or the like, is changed, so that the operation parameters of the acceleration-related devices, such as the electromagnets 22 (22a, 22b, 22c, 22d) and the like, that constitute the synchrotron 21, are changed temporally.

At the timing where the particle beam in the synchrotron 21 reaches a specified kinetic energy and thus the extraction of the particle beam becomes allowable, the particle beam is sent out by an emission device 24 to a high-energy beam transport system. The particle beam introduced into the high-energy beam transport system is properly guided to the treatment room 2 by the actions of the deflection electromagnets 25 to 27 and the like.

Though not shown in the figure, when the high-energy beam transport system has a rotary gantry, the rotary gantry is set at a specified angle, and the particle beam is transported therethrough. Each of sub-systems that constitute the accelerator has a beam monitor, so that the condition of the particle beam is monitored appropriately using the monitor.

The particle beam transported to the treatment room 2 is configured so that it is matched to the shape of the diseased site of the patient 201 fastened to a patient table 203 and its peak position in absorbed dose is matched to the depth of the diseased site, through processes, such as, scanning in a direction perpendicular to the particle beam travel axis, scattering, momentum distribution, collimation, compensation and the like, by unshown irradiation devices, such as a wobbler electromagnet or scanning electromagnet, a scatterer, a ridge filter, a multileaf collimator, a bolus and the like. The configured particle beam is subjected to dose application to the patient 201.

The amount of the particle beam applied to the patient 201 is monitored by the dose monitoring system 5 included in the irradiation devices 202, and the particle beam irradiation is performed until the applied dose reaches a specified dose value. The particle beam irradiation is performed according to the treatment plan, and the treatment plan includes at least one irradiation condition containing abeam condition of the particle beam, settings of the irradiation devices and an irradiation dose value.

When one treatment plan includes plural irradiation conditions and there are two or more kinds of beam conditions contained in the irradiation conditions, an irradiation dose is applied that is specified in the irradiation condition corresponding to a given one of the beam conditions, and thereafter, the setting of the accelerator is changed so as to correspond to the next beam condition and the irradiation is started in the next irradiation condition. This operation is repeated until the irradiation doses specified in all of the irradiation conditions included in the treatment plan are applied.

Next, a series of operations based on the treatment plan of the particle beam therapy apparatus 100 according to Embodiment 1, from preparation for irradiation to completion of irradiation, will be described with reference to FIG. 1. First, the irradiation controller 4 controls the irradiation devices 202 and the dose monitoring system 5 to set the parameters based on the treatment plan.

With respect to the dose monitoring system 5, the irradiation controller transmits to the dose-monitoring system controller 54, an administration dose value and a protective-interruption dose value, at once. The dose monitoring system 5 that received the administration dose value and the protective-interruption dose value, sets the administration dose value and the protective-interruption dose value in the dose monitor circuits 52, 53 in the two sets, respectively, and then notifies the irradiation controller 4 about the completion of setting.

Upon receiving the notifications about setting from all of the irradiation devices 202 including the dose monitoring system 5, the irradiation controller 4 starts the irradiation. With the start of the irradiation, the beam is transported from the accelerator 1 to the treatment room 2, and passes through the irradiation devices 202 including the dose monitoring system 5, so that the beam is radiated to the patient 201. At the time the beam passes through the dose monitoring system 5, the dose monitors 50, 51 transmit the respective amounts of charges by the beam passed therethrough, as monitor signals, to the dose monitor circuits 52, 53, respectively.

Each of the dose monitor circuits 52, 53 that received the monitor signals, processes the monitor signal by pre-calibrated steps to thereby convert it into a dose amount and then integrates it from the starting time of the irradiation. If the integrated dose amount becomes equal to or more than a set interruption dose value, the dose monitor circuit 52 or 53 outputs an interruption signal to the beam controller 3 to thereby reduce the beam radiation, and transmits to the dose-monitoring system controller 54, notification of interruption state informing that the irradiation of the patient 201 with the beam reaches the set dose value, and the irradiation dose amount.

At the same time, the beam controller 3 notifies the dose-monitoring system controller 54 about the reception of such an interruption order from the dose monitor circuit 52 or 53.

The dose-monitoring system controller 54 that received the notification of interruption state and the irradiation dose amount from the dose monitor circuits 52 or 53, transmits the irradiation dose amount to the irradiation controller 4. The irradiation controller 4 confirms that the received irradiation dose amount satisfies the administration dose value, so that a series of irradiation steps are completed. If the irradiation dose amount is less than the administration dose value, the user determines whether to perform re-irradiation or to make a treatment plan again, in consideration of the situation.

Figure 2:
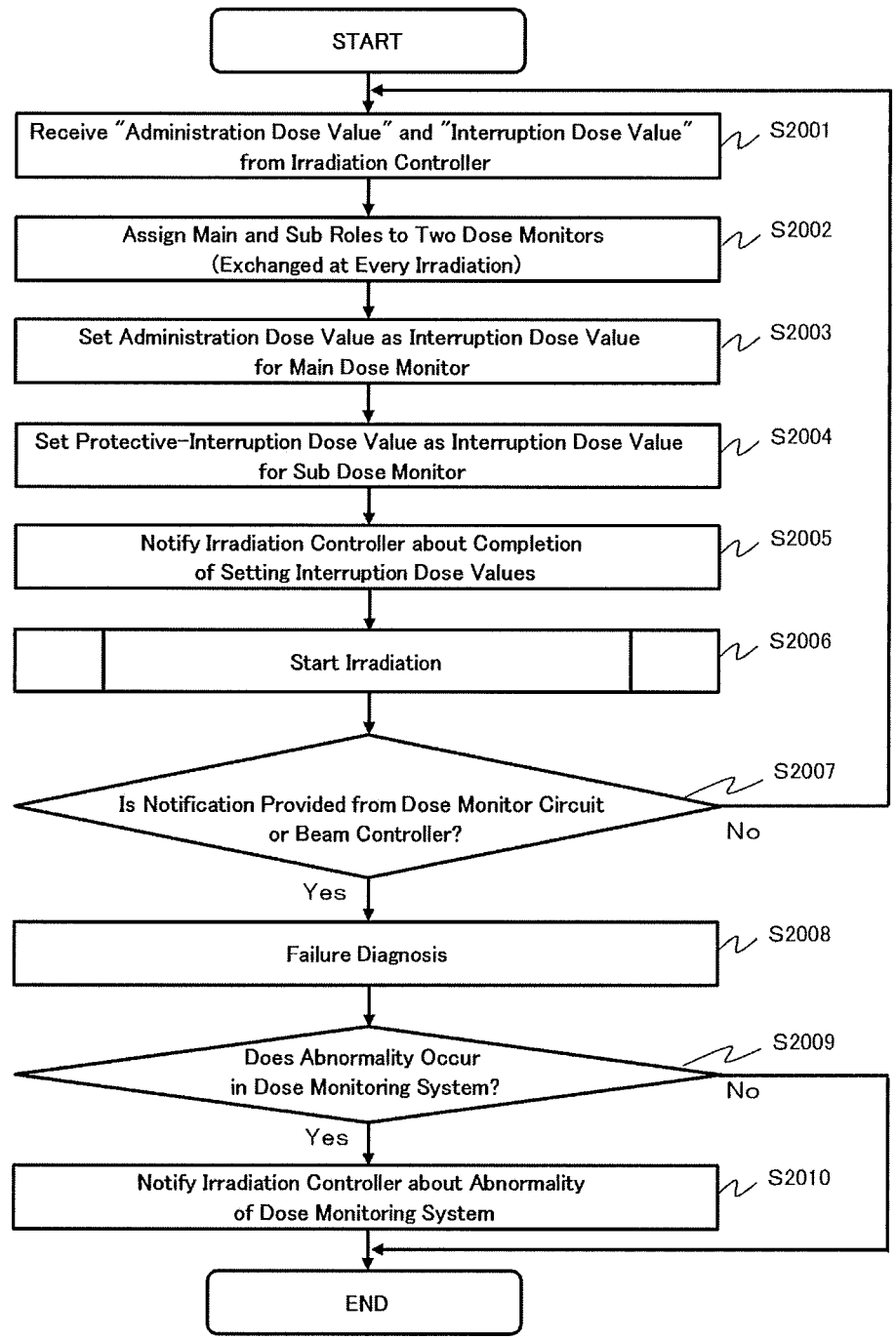
FIG. 2 is a flowchart showing an operational sequence of a dose-monitoring system controller in the particle beam therapy apparatus according to Embodiment 1 of the invention.

Next, operations of the dose-monitoring system controller 54 that represent the feature of the invention in Embodiment 1, will be described in detail based on FIG. 2. First, the dose-monitoring system controller 54 receives the administration dose value and the protective-interruption dose value from the irradiation controller 4 (S2001).

Subsequently, the dose-monitoring system controller 54 controls the dose monitor circuit 52 and the dose monitor circuit 53 so that the roles as a main dose monitor A and a sub dose monitor B are assigned to one and the other of the dose monitor 50 and the dose monitor 51 (S2002).

It should be noted that the main dose monitor A and the sub dose monitor B are set in such a manner that the roles at the next irradiation become different from the roles set last time, so that the roles are exchanged with each other at every irradiation. Here, it is assumed that, initially, the dose monitor 50 is assigned the role as the main dose monitor A, and the dose monitor 51 is assigned the role as the sub dose monitor B.

Then, in order for the dose monitor 50 as the main dose monitor A to detect an interruption dose value for the first role, the dose-monitoring system controller 54 sets the administration dose value as said interruption dose value in the dose monitor circuit 52 that controls the dose monitor 50 (S2003).

Meanwhile, in order for the dose monitor 51 as the sub dose monitor B to detect an interruption dose value for the second role, the dose-monitor system controller 54 sets the protective-interruption dose value as said interruption dose value in the dose monitor circuit 53 that controls the dose monitor 51 (S2004). The dose monitor circuits 52, 53 in which their respective interruption dose values are set, clear their respective dose amounts integrated so far, to thereby get ready for newly integrating the dose amount of the beam.

After the completion of setting the respective interruption dose values in the dose monitor circuits 52, 53, the dose-monitoring system controller 54 notifies the irradiation controller 4 about the completion of setting (S2005). The irradiation controller 4 that received the notification about the completion of setting starts the irradiation of the beam after receiving information about the completion of setting of the other devices and a user's order for starting the irradiation (S2006).

The beam irradiation controller 3 that received the order for starting the irradiation of the beam controls the accelerator 1 to emit the beam, so that the beam is outputted from the accelerator 1 and radiated to the patient 201 after passing through the irradiation devices 202. Because of the radiation of the beam, a monitor signal is outputted from the dose monitor 50 as the main dose monitor A, and the dose amount is integrated in the dose monitor circuit 52.

In the case where all of the devices and inter-device communications are normal, firstly, when in the dose monitor circuit 52 of the dose monitor 50 as the main dose monitor A, the integrated dose amount reaches the administration dose value as the interruption dose value, an interruption order is outputted from the dose monitor circuit 52 to the beam controller 3.

As a result, the beam is stopped from being outputted from the accelerator 1 and thereafter, no monitor signal is outputted from the dose monitor circuit 52 of the dose monitor 50 as the main dose monitor A, so that there is no case where the dose monitor circuit 53 of the dose monitor 51 as the sub dose monitor B outputs an interruption signal.

At the same time, a notification that the dose monitor circuit 52 of the dose monitor 50 as the main dose monitor A has outputted the interruption signal, is provided from the beam controller 3 to the dose-monitoring system controller 54.

In such a case, the dose-monitoring system controller 54 determines that the dose monitor 50 as the main dose monitor A and the dose monitor circuit 52 have operated properly and that a proper response has also been provided from the beam controller 3, and then terminates its operation after notifying the irradiation controller 4 that the irradiation has been properly completed.

In this case, however, the dose monitor 51 as the sub dose monitor B and the dose monitor circuit 53 are not at all involved in the operations for interruption, so that the communicative integrity related to the sub dose monitor B and the communication part of the sub dose monitor B is not confirmed.

After the completion in a state where all of the devices and inter-device communications are normal, in the following irradiations, as described previously, the main dose monitor A and the sub dose monitor B are set in such a manner that the roles become different from the roles set last time, to thereby exchange the roles of the dose monitor 50 and the dose monitor 51 with each other at every irradiation, and then, the steps S2001 to S2006 are similarly repeated.

Here, in the next irradiation, the dose monitor 51 is assigned the role as the main dose monitor A, and the dose monitor 50 is assigned the role as the sub dose monitor B. Accordingly, in the next irradiation, when it is completed in a state where all of the devices and inter-device communications are normal, the communicative integrity is confirmed with respect to the dose monitor 51 as the main dose monitor A and the dose monitor circuit 53.

As the result, with the configuration in which the main and sub roles of two dose monitors 50, 51 are replaced with each other at every radiation, it becomes possible to perform operation checking of the two dose monitors during a therapeutic flow, without the need of a special operation. Further, it becomes possible to certainly detect and specify a failure portion by two radiation steps unless the monitors both fail at the same time.

Further, because the two dose monitors 50, 51 are used alternately, such a failure diagnosis function can also be combined that compares the dose amounts of the two dose monitors to each other at the time of operation of beam interruption, and determines an abnormality in interruption ability if the measured dose amounts are the same or the difference between the measured dose amounts is a threshold value or less, or an abnormality in measurement ability if the difference between the measured dose amounts exceeds a threshold value. This makes it possible to prompt the user to early confirm the failure and take corrective action.

Meanwhile, if a failure occurs in the dose monitor 50 as the main dose monitor A or in the dose monitor circuit 52, so that an interruption signal can not be outputted to the beam controller 3, the dose monitor circuit 53 of the dose monitor 51 as the sub dose monitor B outputs an interruption signal to the beam controller 3 after detecting that the integrated dose amount has reached the protective-interruption dose value.

The dose-monitoring system controller 54 receives from the dose monitor circuit 53 of the dose monitor 51 as the sub dose monitor B, a notification about the operation of the interruption, and receives from the beam controller 3, a notification that an interruption order has been provided from the dose monitor circuit 53.

From this, the dose-monitoring system controller 54 finds that, although an abnormality occurs in the dose monitor 50 as the main dose monitor A or in the dose monitor circuit 52, the dose monitor 51 as the sub dose monitor B and the dose monitor circuit 53 operate properly, and notifies the irradiation controller about the abnormality.

On the other hand, when the dose monitor 50 as the main dose monitor A and the dose monitor circuit 52 operate properly but an abnormality occurs in the communication path from the dose monitor circuit 52 to the beam controller 3, the notification about the operation of the interruption is provided from the dose monitor circuit 52 to the dose-monitoring system controller 54; however, the notification that an interruption order has been provided from the dose monitor circuit 52, is not provided from the beam controller 3. However, because the beam is stopped properly, no notification about the operation of the interruption is provided from the dose monitor circuit 53 of the dose monitor 51 as the sub dose monitor B.

In this manner, the presence/absence of the notification about the operation of the interruption to the dose-monitoring system controller 54 from each of the dose monitor circuits 52, 53 of the main dose monitor A and the sub dose monitor B, and the presence/absence of the notification about each interruption-operation order from the beam controller 3 to the dose-monitoring system controller, are determined (S2007), so that the failure diagnosis is executed about the communication-state integrity between the dose monitoring system 5 and the beam controller 3 (S2008).

In FIG. 3, an example of failure-diagnosis information is shown that corresponds to the conditions of the presence/absence of the notification about the operation of the interruption to the dose-monitoring system controller 54 from each of the dose monitor circuits 52, 53 of the main dose monitor A and the sub dose monitor B, and the presence/absence of the notification about each interruption-operation order from the beam controller 3 to the dose-monitoring system controller. The failure-diagnosis information as shown in FIG. 3 is stored, for example, in a memory in the dose-monitoring system controller 54, or the like.

Based on the failure-diagnosis information as shown in FIG. 3, the dose-monitoring system controller 54 can determine the presence/absence of abnormality in the dose monitoring system 5, from the presence/absence of the notification about the operation of the interruption from each of the dose monitor circuits 52, 53 of the main dose monitor A and the sub dose monitor B, and the presence/absence of the notification about each interruption-operation order from the beam controller 3 (S2009). When it is determined that there is an abnormality, the dose-monitoring system controller transmits the diagnosis result to the irradiation controller 4 (S2010), so that it is possible to promptly notify the user about a specific failure condition.

As described above, the particle beam therapy apparatus according to Embodiment 1 of the invention is configured so that, by the dose-monitoring system controller 54, the main and sub roles of the two dose monitors 50, 51 are switched therebetween at every radiation and their corresponding dose monitor circuits are controlled accordingly. Thus, operation checking of the two dose monitors can be performed during a therapeutic flow, without the need of a special operation. Further, it becomes possible to certainly detect and specify a failure portion by two radiation steps unless the monitors both fail at the same time.

Furthermore, it is possible not only to reduce the confirmation work time for other than the treatment to thereby improve the utilization efficiency of the particle beam therapy apparatus, but also to certainly detect a failure of one of the dose monitors unless the two dose monitors both fail at the same time. Thus, it is possible to prevent excessive irradiation without the need of an additional special failure-diagnosis device.

Further, because the two dose monitors 50, 51 are used alternately, such a failure diagnosis function can also be combined that compares the dose amounts of the two dose monitors to each other at the time of operation of beam interruption, and determines an abnormality in interruption ability if the measured dose amounts are the same or the difference between the measured dose amounts is a threshold value or less, or an abnormality in measurement ability if the difference between the measured dose amounts exceeds a threshold value. This makes it possible to prompt the user to early confirm the failure and take corrective action.

Further, based on the pre-stored failure-diagnosis information, the presence/absence of abnormality and the failure condition in the dose monitoring system 5 are determined by the dose-monitoring system controller 54 from the presence/absence of the notification about the operation of the interruption from each of the dose monitor circuits 52, 53 of the main dose monitor A and the sub dose monitor B, and the presence/absence of the notification about each interruption-operation order from the beam controller 3. Thus, it is possible to promptly notify the user about a more specific failure condition.

It should be noted that appropriate modification and omission in the embodiment may be made in the present invention without departing from the scope of the invention.

DESCRIPTION OF REFERENCE NUMERALS AND SIGNS

1: accelerator, 3: beam controller, 21: synchrotron, 50: dose monitor, 51: dose monitor, 52: dose monitor circuit, 53: dose monitor circuit, 54: dose-monitoring system controller, 100: particle beam therapy apparatus, 202: irradiation devices.

The invention claimed is:

1. A particle beam therapy apparatus comprising:
an accelerator that emits a particle beam after accelerating it using a synchrotron;
an irradiation device that radiates the particle beam emitted from the accelerator to an irradiation target;
a first dose monitor and a second dose monitor each for detecting a dose amount of the particle beam radiated from the irradiation device; and
a dose-monitoring system controller that controls the first dose monitor and the second dose monitor by assigning a first role of detecting a dose amount corresponding to an administration dose value and a second role of detecting a dose amount corresponding to an interruption dose value, to these monitors in a switched manner therebetween at every radiation.

2. The particle beam therapy apparatus according to claim 1, further comprising a beam controller that, when the first dose monitor or the second dose monitor that is assigned the first role detects that an integrated dose amount of the particle beam radiated to the irradiation target is equal to or more than the administration dose value, receives an interruption signal from a dose monitor circuit of the first dose monitor or the second dose monitor that is assigned the first role, to thereby control emission of the particle beam from the accelerator.

3. The particle beam therapy apparatus according to claim 2, wherein, when the beam controller can not receive the interruption signal from the dose monitor circuit of the first dose monitor or the second dose monitor that is assigned the first role, and the second dose monitor or the first dose monitor that is assigned the second role detects that an integrated dose amount of the particle beam radiated to the irradiation target is equal to or more than the interruption dose value, the beam controller receives an interruption signal from a dose monitor circuit of the second dose monitor or the first dose monitor that is assigned the second role, to thereby control emission of the particle beam from the accelerator.

4. The particle beam therapy apparatus according to claim 3, wherein the dose-monitoring system controller performs failure diagnosis, based on pre-stored failure-diagnosis information, according to a notification informing that the beam controller has received the interruption signal from the dose monitor circuit of the first dose monitor or the second dose monitor that is assigned the first role or a notification informing that the beam controller has received the interruption signal from the dose monitor circuit of the second dose monitor or the first dose monitor that is assigned the second role, and a notification informing that the interruption signal has been transmitted from the dose monitor circuit of the first dose monitor or the dose monitor circuit of the second dose monitor, to the beam controller.

* * * * *